United States Patent [19]

Ramachandran et al.

[11] Patent Number: 5,177,225

[45] Date of Patent: Jan. 5, 1993

[54] PROCESS FOR THE PRODUCTION OF ALKYLENE OXIDE

[75] Inventors: Ramakrishnan Ramachandran, Allendale; Donald L. MacLean, Annandale, both of N.J.

[73] Assignee: The BOC Group, Inc., Murray Hill, N.J.

[21] Appl. No.: 549,886

[22] Filed: Jul. 9, 1990

[51] Int. Cl.$^5$ .......................................... C07D 301/08
[52] U.S. Cl. ................................. 549/534; 549/536; 585/821
[58] Field of Search ................. 549/534, 536; 585/821

[56] References Cited

U.S. PATENT DOCUMENTS

| Re. 20,370 | 5/1937 | Lefort | 549/534 |
|---|---|---|---|
| 2,125,333 | 8/1938 | Carter | 549/534 |
| 2,270,780 | 1/1942 | Berl | 549/534 |
| 3,091,622 | 5/1963 | Courter et al. | 549/534 |
| 3,119,837 | 1/1964 | Kingsley et al. | 549/534 |
| 4,498,910 | 2/1985 | Benkmann | 585/821 |
| 4,769,047 | 9/1988 | Dye | 585/821 |

Primary Examiner—C. Warren Ivy
Assistant Examiner—Ba K. Trinh
Attorney, Agent, or Firm—Coleman R. Reap; Larry Cassett

[57] ABSTRACT

Disclosed is a process for the production of an alkylene oxide in which an alkene, and an oxygen containing gas are reacted in the presence of a flame suppressor under conditions of low alkene conversion and high alkylene oxide selectivity in which unreacted alkene is recycled to the reactor and there is efficient removal of nitrogen and carbon dioxide.

16 Claims, 2 Drawing Sheets

PROCESS FOR THE PRODUCTION OF ALKYLENE OXIDE

TECHNICAL FIELD

The present invention is directed to a process for the production of alkylene oxides from alkenes and an oxygen-containing gas in which unreacted alkenes are recovered and recycled to improve the process efficiency and the off-gases are treated without incineration which saves natural resources and provides for the accumulation of carbon dioxide as a by-product.

BACKGROUND OF THE PRIOR ART

The production of alkylene oxides from alkenes in the presence of suitable catalysts is well known. Brian J. Ozero, *Handbook of Chemicals Production Processes*, edited by Robert Meyers, McGraw Hill Book Co. (1986) at Chapter 1.5, discloses cyclic processes using both oxygen and air as an oxidant for the production of ethylene oxide from ethylene. In these processes, the alkene is oxidized in a multitubular catalytic reactor in vapor phase. The reactor off gases are cooled and scrubbed with water in an absorber to recover ethylene oxide which is sent to a recovery section for further purification.

In the oxygen-based process described by Ozero, the scrubber off gases are divided into three parts which are respectively: i) recycled to the reactor, ii) vented and iii) sent to a separator for carbon dioxide removal and recycle of the remaining hydrocarbons. This process suffers from several disadvantages. In particular, the process requires a separate carbon dioxide removal unit and a purge to remove argon which would otherwise accumulate in the system.

In the air-based process described by Ozero, the scrubber off gases are sent to a second reactor, which is the purge reactor, where additional unreacted ethylene is reacted using a higher air to ethylene ratio, thereby foregoing some ethylene oxide selectivity. The reactor off gases are passed through another water scrubber to recover ethylene oxide.

It is known that the volume of hydrocarbons purged, when utilizing air as a source of oxygen, requires that the purge scrubber off gases be incinerated to remove any remaining hydrocarbons in order to meet environmental regulations. In this air-based process, an additional purge oxidation reactor, a water scrubber, and an effluent incinerator are required, as well as a greater volume of catalyst. Another shortcoming of the processes described by Ozero is that they are for practical purposes limited to the use of either oxygen or air. It would be advantageous to eliminate the purge and additional carbon dioxide separator and operate the ethylene oxide reactor at a higher selectivity to improve the overall process efficiency.

SUMMARY OF THE INVENTION

The present invention is directed generally to a process for the production of alkylene oxides by the reaction of an alkene and an oxygen-containing gas. The process of the present invention employs a separation system in which substantially all of the unreacted alkene is removed from the scrubber off gases and recycled back to the reactor. This enables the reaction to be conducted at low conversion, high selectivity while the separation system off gases may be vented directly. Specifically, the present invention is directed to a process for the production of an alkylene oxide from a corresponding alkene which comprises feeding the alkene, an oxygen containing gas and a flame suppressor to a reaction zone. This flame suppressor can be fed either continuously or only during start-up. The gases are reacted under conditions of low alkene conversion and high alkylene oxide selectivity to produce a mixture of alkylene oxide and off gases.

As used herein, the term "low conversion" and "high selectivity" means rates of conversion and selectivity which are respectively lower and higher than processes typically practiced in the prior art. More specifically, the term "low conversion" is a rate of conversion which results in an increase in the rate of selectivity of at least 1% compared to conventional once-through process which do not recycle the alkene to the oxidation reactor. By way of example only, the rates typically employed in the present invention for the conversion of alkene to alkylene oxide are in the range of from about 5 to 80% most typically from about 10 to 60%. Corresponding selectivity rates are in the range from about 50 to 90% for ethylene oxide and 15 to 80% for propylene oxide.

The mixture is quenched to remove the alkylene oxide produced for further purification in a manner known to those skilled in the art.

The remaining off gases are sent to at least one separator, either with or without compression, to produce a first stream containing unreacted alkene and the flame suppressor and a second stream containing the remaining gases. The first stream is recyled back to the reactor to be combined with fresh oxygen-containing gas and fed into the reactor. The second stream is removed and may be vented, incinerated or further separated to remove purified carbon dioxide.

In accordance with the present invention oxygen-enriched air can be used as the oxidant because the system provides for the effective removal of nitrogen gas while taking advantage of the positive effects of conducting the process under high alkylene oxide selectivity at low alkene conversion rates.

In addition, the efficient removal of nitrogen and carbon dioxide from the system reduces the outlay for capital equipment by making the flow rates lower and thereby eliminating the need for a separate carbon dioxide removal system.

Further, when oxygen enriched air is used as the oxidant in the present invention, it is not necessary to use methane to render the reactants inflammable as customarily employed in prior art systems based on oxygen. This is because the nitrogen present in the air and the recycled carbon dioxide provide sufficient flame suppression without undesirable nitrogen gas build-up.

BRIEF DESCRIPTION OF THE DRAWINGS

The following drawings in which like reference characters indicate like parts are illustrative of embodiments of the invention and are not intended to limit the invention as encompassed by the claims forming part of the application. In particular, the embodiments are described in connection with the production of ethylene oxide from ethylene. It should be understood, however, that such embodiments are applicable to the production of propylene oxide from propylene and the like.

DETAILED DESCRIPTION OF THE INVENTION

Figure 1:
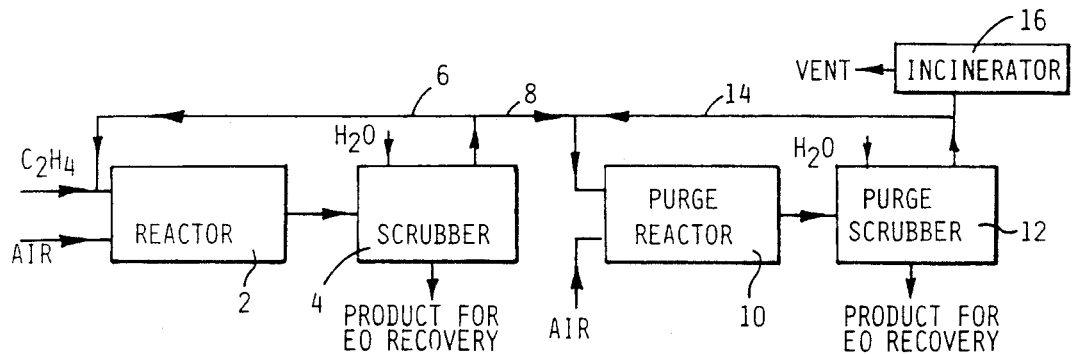
FIG. 1 is a schematic view of a prior art system for converting ethylene to ethylene oxide using air as the oxidant.

Prior processes for the production of ethylene oxide by the oxidation of ethylene have employed either air or pure oxygen as the oxidant. FIG. 1 shows a prior art system using air as the oxidant and a purge to remove the inert gases to prevent nitrogen build up and an incinerator to meet environmental regulations.

Specifically air and ethylene are fed to an oxidation reactor 2 containing a catalyst composed, for example, of a metal on a support such as silver on alumina. A mixture of ethylene oxide and off gases are cooled and then fed to a scrubber 4 in which water is used to dissolve the ethylene oxide for subsequent treatment. The off gases including unreacted ethylene are removed and divided into two streams. A first stream is returned via a line 6 to the oxidation reactor 2 while a second stream is sent via a line 8 to a purge reactor 10.

The second stream containing off gases including oxygen, nitrogen, argon, ethylene and carbon dioxide is combined with additional quantities of air in the purge reactor 10 to provide a relatively high oxygen to ethylene ratio which obtains a higher conversion of ethylene and thereby produces additional quantities of ethylene oxide. The by-products of the reaction are sent to a second scrubber 12 in which ethylene oxide is recovered and a stream of off gases containing unreacted ethylene is divided into two streams.

A first stream is fed via a line 14 back to the purge reactor 10 and the second stream is sent to an incinerator 16, where the off-gases, particularly the hydrocarbons contained therein, are combusted and thereafter vented.

Figure 2:
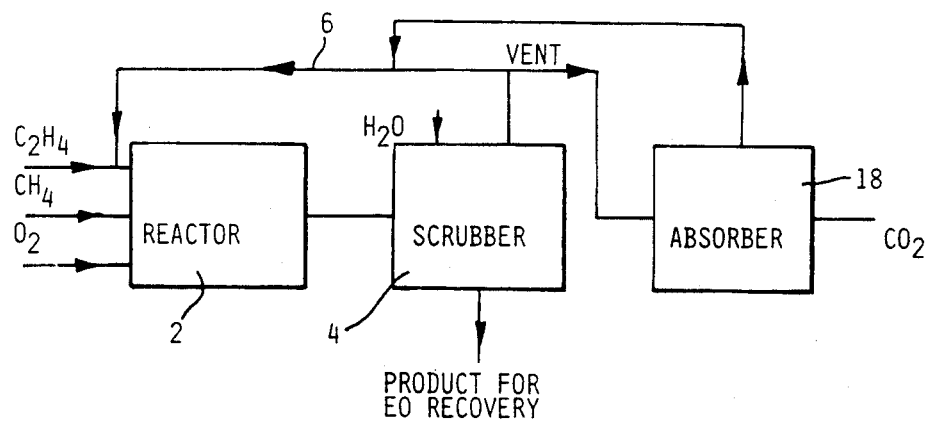
FIG. 2 is a schematic view of a prior art system for converting ethylene to ethylene oxide using pure oxygen as the oxidant.

Referring to FIG. 2, there is shown a prior art system in which pure oxygen gas is used as the oxidant. Ethylene, oxygen and a flame suppressor such as methane gas are sent to the oxidation reactor 2 of the same type described in connection with FIG. 1. Ethylene oxide and off gases are sent to the scrubber 4 for recovery of ethylene oxide for purification. The off-gases are divided into three streams, one stream flows via the line 6 back to the oxidation reactor 2. A second stream is sent to an incinerator for combusting the hydrocarbons and a third stream is sent to an absorber 18 for removing carbon dioxide from the off gases. A portion of the off gases removed from the absorber 18 is sent to the oxidation reactor 2 and the remaining off gases are recycled to the absorber 18.

In accordance with the present invention, there is provided a system for the conversion of an alkene to an alkylene oxide in which the oxidant can be selected from any one or more of pure oxygen, air and oxygen enriched air. The oxidants can be combined and the composition of the oxidants can be changed without the need for material changes in capital equipment depending on the alkylene oxide requirement. As a consequence, the system of the present invention provides greater flexibility in the use of oxidants over known systems.

Figure 3:
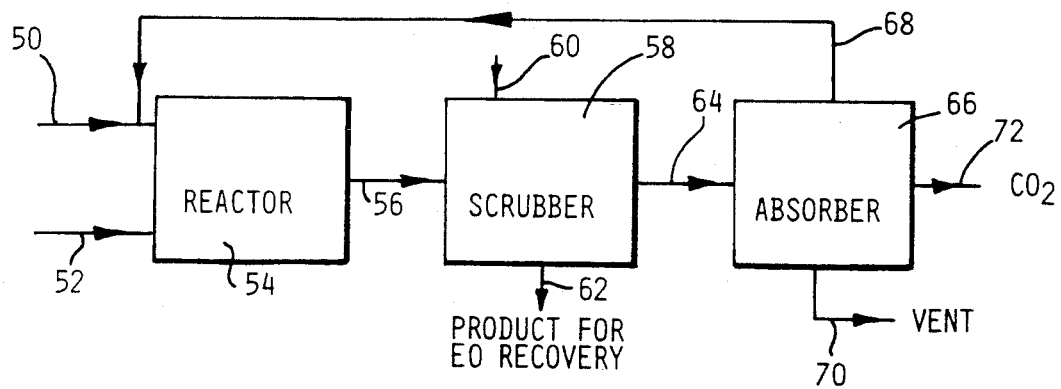
FIG. 3 is a schematic view of an embodiment of the present invention for converting an alkene to the corresponding alkylene oxide using pure oxygen or other oxygen-containing gas as the oxidant.

Referring to FIG. 3, the process of the present invention commences by forwarding a gaseous alkene via a line 50 and an oxygen containing gas via a line 52 to an oxidation reactor 54. The starting alkenes have from 2 to 4 carbon atoms, particularly ethylene and propylene.

The oxidation reactor contains a suitable oxidation catalyst, such as silver on alumina, in a fixed, fluidized or slurry reactor. The catalyst may be promoted with other known metals to improve stability and selectivity.

As previously indicated, the oxidant may range from pure oxygen to air. The optimum oxygen concentration will depend on whether the process is used to retrofit an existing plant or implemented as a new plant or, if retrofitted, the need for additional capacity. In other words, the process can be employed without major modifications in plants of varying capacity.

It is also necessary in accordance with the present invention to provide for a flame suppressor. In the case of pure oxygen, methane or ethane may be used as a flame suppressor. The amount of the flame suppressor is controlled so as to avoid the formation of flammable mixtures in the system. Typically, the total amount of flame suppressors is in the range of about 20 to 80%. A major portion of the flame suppressor is added only during the start up since most of the flame suppressor is recycled. For the process using air as the oxygen containing gas, typical nitrogen concentrations are about 30% by volume and carbon dioxide concentrations about 20% as the reactor feed.

The oxidation reaction is conducted at a temperature in the range of from about 200° to 500° C. and a pressure of from about 15 to 400 psig.

The resulting product mixture includes the alkylene oxide (e.g. ethylene oxide) unreacted alkene (e.g. ethylene), oxygen and carbon dioxide, nitrogen, and argon if other than pure oxygen is used as the oxidant.

The mixture is cooled in a cooler (not shown) and then sent via the line 56 to a scrubber 58 wherein water from a line 60 is used to separate the alkylene oxide from the off gases. The alkylene oxide is removed from the scrubber 58 through a line 62.

The off gases are sent via a line 64 to a pressure swing adsorber 66 containing two or more beds, preferably in parallel with suitable adsorbents capable of removing carbon dioxide, nitrogen and argon, if present in the reactor feed. Typical adsorbents include activated carbon, silica gel and molecular sieves and other adsorbents well known to those skilled in the art. The scrubber off gases enter the adsorber 66 at a temperature of from about 10° to 100° C. and a pressure of from about 0 to 400 psig. Depending upon the reactor pressure, it may be necessary to compress the scrubber off gases before feeding it to the pressure swing adsorber 66.

A first stream exits the adsorber 66 via a line 68 for return to the oxidation reactor 54. The first stream contains substantially all of the unreacted alkylene and minor amounts of carbon dioxide, nitrogen, oxygen and argon.

Because substantially all of the hydrocarbons (e.g. ethylene) leaving the adsorber 66 are returned in the recycle, a second stream containing off gases excluding hydrocarbons can be vented via the line 70 without incineration. As a consequence, the process of the present invention can operate without the costly incineration apparatus associated with prior art processes.

Carbon dioxide can be removed as part of the vent gases or separated from the vent gases and removed as a by-product via a line 72 depending upon the oxygen concentration in the reactor feed. If air is used as the oxygen containing gas, carbon dioxide may not be recovered as a by-product. The separation of carbon dioxide from the vent gases requires a carbon dioxide adsorbing material such as molecular sieve. Carbon dioxide is removed by adsorbing it on the molecular sieve preferentially over the remaining gases and is obtained as a desorbed product.

When air is used as the oxygen containing gas or when very large quantities of carbon dioxide must be removed, it may be desirable to use more than one pressure swing adsorption system in series. The first system preferably is capable of selectively adsorbing carbon dioxide while the second preferentially adsorbs hydrocarbons.

Figure 4:
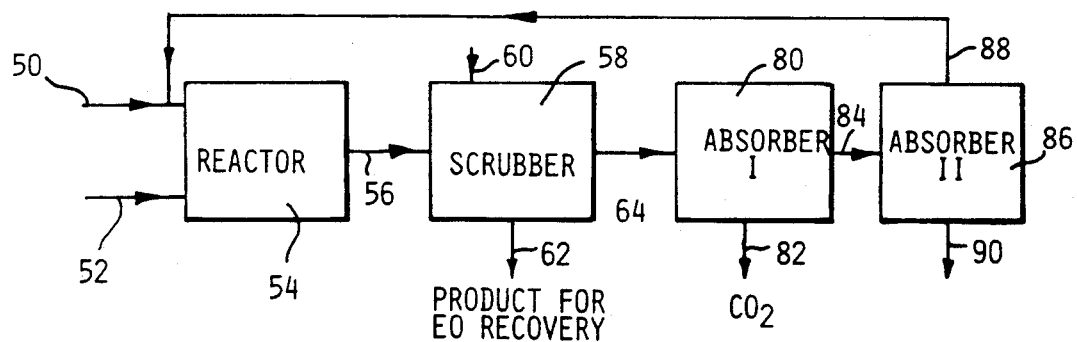
FIG. 4 is a schematic view of another embodiment of the present invention similar to the embodiment shown in FIG. 3 in which multiple adsorbers are used for separation.

Referring to FIG. 4, there is shown the use of two pressure swing adsorption columns. The off gases from the scrubber 58 are sent via the line 64 to a first pressure swing adsorber 80 containing adsorbents which preferentially adsorb carbon dioxide as described previously. Carbon dioxide is removed as a by-product via a line 82. The remaining off gases are sent via a line 84 to a second pressure swing adsorber 86 containing adsorbents which preferentially remove hydrocarbons (e.g. ethylene) from the off gas stream via a line 88 for recycling. Nitrogen, oxygen and other off gases can be vented from the second pressure swing adsorber 86 via a line 90 without incineration.

EXAMPLE 1

The process of the present invention was conducted in accordance with FIG. 3 in the following manner to produce ethylene oxide. 141 moles of ethylene, and 1203.5 moles of air (containing 252.6 moles of oxygen, 950.2 moles of nitrogen and a trace amount of ethylene) were forwarded via the lines 50, 52 respectively into the oxidation reactor 54. In addition, the reactor 54 was supplied with a recycle of ethylene and other off gases via the line 68 to raise the quantity of the gases therein to that shown in Table 1.

TABLE 1

| CONTENTS TO THE REACTOR | | |
|---|---|---|
| Gas | Moles | % by volume |
| ethylene | 1293.7 | 35.7 |
| ethane | 72.4 | 2.0 |
| oxygen | 281.2 | 7.8 |
| carbon dioxide | 792.9 | 21.9 |
| nitrogen | 1187.8 | 32.7 |

The gas mixture set forth in Table 1 produces the gas mixture shown in Table 3 as the product. This product was forwarded via the line 56 to the scrubber 58.

TABLE 2

| CONTENTS TO THE SCRUBBER | | |
|---|---|---|
| Gas | Moles | % by volume |
| ethylene | 1164.3 | 32.5 |
| ethane | 72.4 | 2.0 |
| oxygen | 143.1 | 4.0 |
| ethylene oxide | 100.0 | 2.8 |
| carbon dioxide | 851.6 | 23.8 |
| water vapor | 58.7 | 1.6 |

TABLE 2-continued

| CONTENTS TO THE SCRUBBER | | |
|---|---|---|
| Gas | Moles | % by volume |
| nitrogen | 1187.8 | 33.2 |

100 moles of ethylene oxide were removed from the scrubber 58 via the line 62 to provide a conversion rate of ethylene to ethylene oxide of 10.0% and a selectivity of 77%.

After quenching, the gases were sent to a pressure swing adsorber 66 to separate ethylene and, optionally carbon dioxide from the off gases. The charge sent to the pressure swing adsorber had the composition shown below in Table 3.

TABLE 3

| CONTENTS TO THE PSA | | |
|---|---|---|
| Gas | Moles | % by volume |
| ethylene | 1164.3 | 33.8 |
| ethane | 72.4 | 2.1 |
| oxygen | 43.1 | 4.2 |
| carbon dioxide | 881.0 | 25.5 |
| nitrogen | 1187.8 | 34.4 |

The temperature in the pressure swing adsorber 66 was in the range from about 15° to 35° C. and a pressure of from about 5 to 100 psig.

Substantially all of the ethylene (1152.7 moles; 99+%) was sent via the line 68 to the oxidation reactor 54. A gas mixture containing 11.6 moles of ethylene, 0.7 moles of ethane, 74.9 moles of oxygen and 88.1 moles of carbon dioxide was vented out of the system via the line 70. Depending upon the hydrocarbon recovery in the pressure swing adsorber, it may be necessary to incinerate the vent stream.

EXAMPLE 2

The process of the present invention was conducted in accordance with FIG. 3 using pure oxygen as the oxidant to produce ethylene oxide. 141.0 moles of ethylene, 213.0 moles of oxygen and a trace amount of ethane was forwarded via the lines 50 and 52, respectively to the oxidation reactor 54. In addition, the reactor 54 was supplied with a recycle of ethylene and other gases via the line 68 to raise the quantity of gases therein to that shown in Table 4.

TABLE 4

| CONTENTS TO THE REACTOR | | |
|---|---|---|
| Gas | Moles | % by volume |
| ethylene | 1293.7 | 54.1 |
| ethane | 72.4 | 3.0 |
| oxygen | 231.7 | 9.7 |
| carbon dioxide | 792.9 | 33.2 |

The gas mixture shown in Table 4 was reacted to produce the stream shown in Table 5 which was forwarded via the line 56 to the scrubber 58.

TABLE 5

| CONTENTS TO THE SCRUBBER | | |
|---|---|---|
| Gas | Moles | % by volume |
| ethylene | 1164.3 | 49.7 |
| ethane | 72.4 | 3.1 |
| oxygen | 93.6 | 4.0 |
| ethylene oxide | 100.0 | 4.3 |
| carbon dioxide | 851.6 | 36.4 |

The ethylene oxide was removed from the scrubber 58 to provide a conversion rate of ethylene to ethylene oxide of 10.0% and a selectivity of 77%.

After quenching the gases were sent to a pressure swing absorber 66 to separate ethylene and, optionally carbon dioxide from the off gases. The charge sent to the pressure swing adsorber had the composition shown below in Table 6.

TABLE 6

| CONTENTS TO THE PSA | | |
|---|---|---|
| Gas | Moles | % by volume |
| ethylene | 1164.3 | 52.7 |
| ethane | 72.4 | 3.3 |
| oxygen | 93.6 | 4.2 |
| carbon dioxide | 881.0 | 39.8 |

The temperature in the adsorber 66 was the range from about 15° to 35° C. and a pressure of from about 5 to 100 psig.

Substantially all of the ethylene (1152.7 moles; 99+% by volume) was sent via the line 68 to the oxidation reactor 54. A gas mixture containing 11.6 moles of ethylene, 0.7 moles of ethane and 74.9 moles of oxygen and 88.1 moles of carbon dioxide was vented out of the system via the line 70. Depending on the amount of hydrocarbon in the stream, it may be necessary to incinerate the vent stream.

EXAMPLE 3

The process of the present invention was conducted in accordance with FIG. 3 in the following manner to produce propylene oxide. 405.1 moles of propylene, 8.3 moles of propane and 558.4 moles of oxygen, were forwarded via the lines 50, 52 respectively into the oxidation reactor 54. In addition, the reactor 54 was supplied with a recycle of propylene and other off gases via the line 68 to raise the quantity of the gases therein to that shown in Table 7.

TABLE 7

| CONTENTS TO THE REACTOR | | |
|---|---|---|
| Gas | Moles | % by volume |
| propylene | 2461.5 | 58.5 |
| propane | 698.9 | 16.6 |
| oxygen | 625.7 | 14.9 |
| carbon dioxide | 336.2 | 8.0 |
| ethylene | 84.9 | 2.0 |
| formaldehyde | 1.9 | 0.0 |

The gas mixture set forth in Table 7 produces the gas mixture shown in Table 8 as the product. This product was forwarded via the line 56 to the scrubber 58.

TABLE 8

| CONTENTS TO THE SCRUBBER | | |
|---|---|---|
| Gas | Moles | % by volume |
| propylene | 2082.5 | 49.7 |
| propane | 698.9 | 16.7 |
| oxygen | 83.8 | 2.0 |
| propylene oxide | 100.0 | 2.4 |
| acetaldehyde | 134.6 | 3.2 |
| formaldehyde | 64.9 | 1.5 |
| carbon dioxide | 594.8 | 14.2 |
| ethylene | 153.8 | 3.7 |
| water vapor | 241.0 | 5.7 |
| Balance (alcohol, acetone, dienes) | 38.0 | 0.9 |

100 moles of propylene oxide were removed from the scrubber 58 via the line 62 to provide a conversion rate of propylene to propylene oxide of 15.4% and a selectivity of 26.4%.

After quenching, the gases were sent to a pressure swing adsorber 66 to separate propylene and, optionally carbon dioxide from the off gases. The charge sent to the pressure swing adsorber had the composition shown below in Table 9.

TABLE 9

| CONTENTS TO THE PSA | | |
|---|---|---|
| Gas | Moles | % by volume |
| propylene | 1300.6 | 52.0 |
| propane | 413.8 | 16.5 |
| oxygen | 82.8 | 3.3 |
| carbon dioxide | 560.3 | 22.4 |
| ethylene | 141.5 | 5.7 |
| formaldehyde | 3.2 | 0.1 |

The temperature in the pressure swing adsorber 66 was in the range from about 15° to 35° C. and a pressure of from about 5 to 100 psig.

1274.6 moles of propylene was sent via the line 68 to the oxidation reactor 54. A gas mixture containing 26.0 moles of propylene, 8.3 moles of propane, 16.6 moles of oxygen, 224.1 moles of carbon dioxide and 56.6 moles of ethylene was vented out of the system via the line 70. Depending upon the hydrocarbon recovery in the pressure swing adsorber, it may be necessary to incinerate the vent stream.

We claim:

1. A process for the production of an alkylene oxide from a corresponding alkene comprising:
   (a) Feeding the alkene, an oxygen containing gas and a flame suppressor to a reaction zone;
   (b) reacting the alkene and oxygen containing gas in said reaction zone under conditions of low alkene conversion and high selectivity to produce a mixture of alkylene oxide and off gases;
   (c) quenching the mixture obtained in step (b) and removing substantially all of the alkylene oxide from said quenched mixture;
   (d) subjecting all of the alkylene oxide-free off-gases in said quenched mixture to pressure swing adsorption with an adsorbent which preferentially adsorbs unreacted alkene, thereby producing a first stream enriched in unreacted alkene and a second stream enriched in carbon dioxide; and
   (e) forwarding all of said first stream to the reaction zone and removing said second stream.

2. The process of claim 1 further comprising venting the second stream.

3. The process of claim 1 further comprising incinerating the second stream.

4. The process of claim 1 further comprising purifying the alkylene oxide removed from the quenched mixture.

5. The process of claim 1 wherein the oxygen containing gas is air and the flame suppressor is a combination of nitrogen gas present in the air and hydrocarbons present in the first stream.

6. The process of claim 1 wherein the oxygen containing gas is selected from oxygen and oxygen enriched air and the flame suppressor is an alkane alone or in combination with nitrogen.

7. The process of claim 1 wherein the total amount of flame suppressor is in the range of about 20 to 80% by volume.

8. The process of claim 1 wherein the alkene is ethylene.

9. The process of claim 1 wherein the alkene is propylene.

10. The process of claim 1 wherein step (c) comprises treating the mixture obtained in step (b) with water.

11. The process of claim 1 wherein the carbon dioxide adsorbent is a carbon molecular sieve.

12. A process for the production of an alkylene oxide from a corresponding alkene comprising:
   (a) Feeding the alkene, an oxygen-containing gas and a flame suppressor to a reaction zone;
   (b) reacting the alkene and oxygen containing gas in said reaction zone under conditions of low alkene conversion and high selectivity to produce a mixture of alkylene oxide and off gases;
   (c) quenching the mixture obtained in step (b) and removing substantially all of the alkylene oxide from said quenched mixture;
   (d) separating the alkene oxide-free off-gases from step (c) into an alkene-enriched stream, a carbon dioxide-enriched stream and a stream enriched in the remaining off-gases by passing all of the off-gases from step (c) through a first pressure swing absorber which contains one of a carbon dioxide absorbent or a hydrocarbon absorbent, then through a second pressure swing adsorber which contains the other of a carbon dioxide absorbent or a hydrocarbon absorbent; and
   (e) forwarding all of the alkene-enriched stream to the reaction zone.

13. The process of claim 12 wherein the carbon dioxide adsorbent is molecular sieve.

14. The process of claim 12 wherein the hydrocarbon adsorbent is selected from molecular sieve, activated carbon, silica gel and mixtures of these.

15. The process of claim 1 wherein the reaction of the alkene and the oxygen containing gas is conducted at a temperature of from about 200° to 500° C. and a pressure of from about 15 to 400 psig.

16. The process of claim 1 wherein the off-gases are separated at a temperature of from about 10° to 100° C. and a pressure of from about 0 to 400 psig.

* * * * *

UNITED STATES PATENT AND TRADEMARK OFFICE
CERTIFICATE OF CORRECTION

PATENT NO. : 5,177,225
DATED : January 5, 1993
INVENTOR(S) : Ramakrishnan Ramachandran and Donald L. MacLean It is certified that error appears in the above—identified patent and that said Letters Patent is hereby corrected as shown below:

Column 10, line 3, delete "absorber" and substitute --adsorber-- therefor.

Column 10, line 4, delete "absorbent" and substitute --adsorbent- therefor.

Column 10, line 4, after hydrocarbon delete "absorbent" and substitute --adsorbent-- therefor.

Column 10, line 6, delete "absorbent" and substitute --adsorbent-- therefor.

Column 10, line 7, delete "absorbent" and substitute -- adsorbent-- therefor

Signed and Sealed this

Second Day of November, 1993

Attest:

BRUCE LEHMAN

Attesting Officer     Commissioner of Patents and Trademarks